US008647612B2

(12) United States Patent
Garner et al.

(10) Patent No.: US 8,647,612 B2
(45) Date of Patent: *Feb. 11, 2014

(54) DITHIOL COMPOUNDS, DERIVATIVES, AND TREATMENT OF PRESBYOPIA

(75) Inventors: William Garner, Eastport, ME (US); Margaret Garner, Eastport, ME (US); Ronald D. Blum, Roanoke, VA (US)

(73) Assignee: Encore Health, LLC, Roanoke, VA (US)

( * ) Notice: Subject to any disclaimer, the term of this patent is extended or adjusted under 35 U.S.C. 154(b) by 656 days.

This patent is subject to a terminal disclaimer.

(21) Appl. No.: 12/390,928

(22) Filed: Feb. 23, 2009

(65) Prior Publication Data

US 2009/0192212 A1 Jul. 30, 2009

Related U.S. Application Data

(63) Continuation-in-part of application No. 12/267,260, filed on Nov. 7, 2008, and a continuation-in-part of application No. 11/946,659, filed on Nov. 28, 2007, now Pat. No. 8,147,816, which is a continuation-in-part of application No. 11/135,271, filed on May 24, 2005, now Pat. No. 7,914,815, which is a continuation-in-part of application No. 10/050,879, filed on Jan. 18, 2002, now Pat. No. 6,923,955, said application No. 11/946,659 is a continuation-in-part of application No. 11/010,436, filed on Dec. 14, 2004, now Pat. No. 7,935,332, which is a continuation of application No. 10/050,879, said application No. 11/946,659 is a continuation-in-part of application No. 10/969,868, filed on Oct. 22, 2004, now abandoned, which is a continuation-in-part of application No. 10/050,879, which is a continuation-in-part of application No. 09/930,287, filed on Aug. 16, 2001, now abandoned.

(60) Provisional application No. 61/033,870, filed on Mar. 5, 2008, provisional application No. 61/060,487, filed on Jun. 11, 2008, provisional application No. 61/077,186, filed on Jul. 1, 2008, provisional application No. 60/861,262, filed on Nov. 28, 2006, provisional application No. 60/907,734, filed on Apr. 16, 2007, provisional application No. 60/924,686, filed on May 29, 2007, provisional application No. 60/574,211, filed on May 26, 2004, provisional application No. 60/262,423, filed on Jan. 19, 2001, provisional application No. 60/225,659, filed on Aug. 16, 2000.

(51) Int. Cl.
*A61K 31/74* (2006.01)

(52) U.S. Cl.
USPC ........................................................ 424/78.04

(58) Field of Classification Search
None
See application file for complete search history.

(56) References Cited

U.S. PATENT DOCUMENTS 3,238,224 A 3/1966 Ohara et al.
3,855,240 A 12/1974 Mueller
(Continued)

FOREIGN PATENT DOCUMENTS

EP 0 369 880 5/1990
WO WO 93/25166 12/1993
(Continued)

OTHER PUBLICATIONS

U.S. Appl. No. 12/815,586, filed Jun. 15, 2010, Garner et al.
(Continued)

*Primary Examiner* — Carlos Azpuru
(74) *Attorney, Agent, or Firm* — Sterne, Kessler, Goldstein & Fox P.L.L.C.

(57) ABSTRACT

Dithiol compounds and derivatives thereof are disclosed. The agents are useful for treating ocular disease, especially presbyopia and cataract.

8 Claims, 5 Drawing Sheets

(56) References Cited

U.S. PATENT DOCUMENTS

| | | | |
|---|---|---|---|
| 4,210,667 A | 7/1980 | Sarges et al. |
| 4,755,528 A | 7/1988 | DuPriest et al. |
| 5,395,356 A | 3/1995 | King et al. |
| 5,459,133 A | 10/1995 | Neufeld |
| 5,465,737 A | 11/1995 | Schachar |
| 5,466,680 A | 11/1995 | Rudy |
| 5,476,515 A | 12/1995 | Kelman et al. |
| 5,488,050 A | 1/1996 | Neufeld |
| 5,503,165 A | 4/1996 | Schachar |
| 5,527,774 A | 6/1996 | Girard |
| 5,529,076 A | 6/1996 | Schachar |
| 5,624,955 A | 4/1997 | Nagasawa et al. |
| 5,665,770 A | 9/1997 | Terao et al. |
| 5,686,450 A | 11/1997 | Hellberg et al. |
| 5,688,828 A | 11/1997 | Hellberg et al. |
| 5,691,379 A | 11/1997 | Ulrich et al. |
| 5,722,952 A | 3/1998 | Schachar |
| 5,817,630 A | 10/1998 | Hofmann et al. |
| 5,843,184 A | 12/1998 | Cionni |
| 5,869,468 A | 2/1999 | Freeman |
| 5,874,455 A | 2/1999 | Terao et al. |
| 5,888,243 A | 3/1999 | Silverstrini |
| 6,007,510 A | 12/1999 | Nigam |
| 6,013,462 A | 1/2000 | Kauvar et al. |
| 6,030,950 A | 2/2000 | Ohlenschlager |
| 6,063,116 A | 5/2000 | Kelleher |
| 6,214,044 B1 | 4/2001 | Silverstrini |
| 6,288,106 B1 | 9/2001 | Pearson et al. |
| 6,313,164 B1 | 11/2001 | Fujita et al. |
| 6,339,102 B1 | 1/2002 | Meyerhoff et al. |
| 6,387,945 B2 | 5/2002 | Packer et al. |
| 6,472,541 B2 | 10/2002 | Tsien et al. |
| 6,664,287 B2 | 12/2003 | Avery et al. |
| 6,703,039 B2 | 3/2004 | Xia et al. |
| 6,743,779 B1 | 6/2004 | Unger et al. |
| 6,923,955 B2 | 8/2005 | Till et al. |
| 7,164,943 B2 | 1/2007 | Roy |
| 2002/0025311 A1 | 2/2002 | Till |
| 2002/0035243 A1 | 3/2002 | Imfeld et al. |
| 2003/0187058 A1 | 10/2003 | Hasselwander et al. |
| 2003/0228299 A1 | 12/2003 | Droy-Lefaix et al. |
| 2004/0044227 A1 | 3/2004 | Klatt et al. |
| 2004/0092586 A1 | 5/2004 | Ogata et al. |
| 2005/0101677 A1 | 5/2005 | Till |
| 2005/0112113 A1 | 5/2005 | Till et al. |
| 2005/0130881 A1 | 6/2005 | Shashoura et al. |
| 2005/0137124 A1 | 6/2005 | Castillejos |
| 2005/0171212 A1 | 8/2005 | Gierhart et al. |
| 2005/0287201 A1 | 12/2005 | Till et al. |
| 2006/0177430 A1 | 8/2006 | Bhushan |
| 2006/0188492 A1 | 8/2006 | Richardson et al. |
| 2007/0055070 A1 | 3/2007 | Lawrence |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0139990 A1 | 6/2008 | Till et al. |
| 2008/0213239 A1 | 9/2008 | Morris |
| 2009/0082281 A1 | 3/2009 | Shashoua |
| 2009/0093541 A1 | 4/2009 | Ogata |
| 2009/0124683 A1 | 5/2009 | Garner et al. |
| 2009/0227677 A1 | 9/2009 | Garner et al. |
| 2010/0098653 A1 | 4/2010 | Yu et al. |

FOREIGN PATENT DOCUMENTS

| | | |
|---|---|---|
| WO | WO 93/25199 | 12/1993 |
| WO | WO 94/01773 | 1/1994 |
| WO | WO 02/13863 | 2/2002 |
| WO | WO 02056804 | 7/2002 |
| WO | WO 03084532 | 10/2003 |
| WO | WO 2004/028536 | 4/2004 |
| WO | WO 2005/084635 | 9/2005 |
| WO | WO 2006/047080 | 5/2006 |
| WO | WO 2007011874 | 1/2007 |
| WO | WO 2008/120070 | 10/2008 |
| WO | WO 2010054135 | 5/2010 |
| WO | WO 2010147962 | 12/2010 |

OTHER PUBLICATIONS

U.S. Appl. No. 12/815,526, filed Jun. 15, 2010, Garner et al.

Bustamante, J., et al., 1998. α-Lipoic Acid in Liver Metabolism and Disease. *Free Radical Biology & Medicine* 24: No. 6 1023-1039.

Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.

Giblin FJ, et al. 1979. The effects of X-irradiation on lens reducing systems. Investigative Ophthalmology & Visual Science 18:468-475.

Kramár P, et al. 1987. Thermal cataract formation in rabbits. NCBI Pubmed abstract, PMID: 3426637, abstract of Bioelectromagnetics 8:397-406.

Li, X., Liu, Z., et al. 2008. Lipoamide protects retinal pigment epithelial cells from oxidative stress and mitochondrial dysfunction. *Free Radic Biol Med.* 44(7): 1465-1474.

Lipman RM, et al. 1988. Cataracts induced by Microwave and Ionizing Radiation. NCBI Pubmed abstract, PMID: 3068822, abstract of Surv. Ophthalmol 33:200-210.

Trayhurn P. and Van Heyningen R. 1973. The Metabolism of Amino Acids in the Bovine Lens; Their Oxidation as a Source of Energy. *Biochem. J.* 136:67-75.

Wakabayashi, Y. et al. 2006. Glutamate Levels in Aqueous Humor of Patients with Retinal Artery Occlusion. *Retina* 26:432-436.

Zwingmann, C. et al. 2001. $^{13}$C Isotopomer Analysis of Glucose and Alanine Metabolism Reveals Cytosolic Pyruvate Compartmentation as Part of Energy Metabolism in Astrocytes. *GLIA* 34:200-212.

Al-Ghoul, K. J., R. K. Nordgren, A. J. Kuszak, C. D. Freel, M. J. Costello, and J. R. Kuszak, 2001. Structural evidence of human nuclear fiber compaction as a function of ageing and cataractogenesis. *Experimental eye research* 72: 199-114.

Applegate, M. A., K. M. Humphries, and L. I. Szweda. 2007. Reversible Inhibition of alpha-Ketoglutarate Dehydrogenase by Hydrogen Peroxide: Glutathionylation and Protection of Lipoic Acid. *Biochemistry*.

M. Argirova, M., M Kleine-Reidick, and W. Breipohl. 2004. Redox status of the ere lens: a regional study. *Cell biochemistry and biophysics* 41: 381-390.

Ariga T, et al. 2000. Antithrombotic and antineoplastic effects of phyto-organosulfur compounds. Biofactors. 13(1-4):251-5.

Arora A, et al. 2004. Reversal of P-glycoprotein-mediated multidrug resistance by diallyl sulfide in K562 leukemic cells and in mouse liver. Carcinogenesis. 25(6):941-9, Epub Jan. 16, 2004.

Asmellash S, et al. 2005. Modulating the endoplasmic reticulum stress response with trans-4,5-dihydroxy-1,2-dithiane prevents chemilly induced renal injury in vivo. Toxicol Sci. 88(2):576-84, Epub Sep. 8, 2005.

Baghieri, S. and M. H. Garner, 1992. Na,K-ATPase and phospholipid degradation in bovine and human lenses. *Current eye research* 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.

Bilska, A., and L. Wlodek, 2005. Lipoic acid—the drug of the future? Pharmacol Rep 57: 570-577.

Bilska, A., M. Dubiel, M. Sokolowska-Jezewicz, E. Lorenc-Koci, and L. Wlodek, 2007. Alpha-lipoic acid differently affects the reserpine-induced oxidative stress in the striatum and prefrontal cortex of rat brain. *Nemscience* 146: 1758-1771.

Bitar, M. S., S. Wahid, C. W. Pilcher, E. Al-Saleh, and F. Al-Mulla. 2004. Alpha-lipoic acid mitigates insulin resistance in Goto-Kekizaid rats. *Hormone and metabolic research. Hormon- und Stoffwechselforschung* 36: 542-549.

Bianco, R. A., T. R. Ziegler, B. A. Carlson, P. Y. Cheng, Y. Park, G. A. Cotsonis, C. J. Accardi, and D. P. Jones. 2007. Diurnal variation in glutathione and cysteine redox states in human plasma. *The American journal of clinical nutrition* 86: 1016-1023.

(56) References Cited

OTHER PUBLICATIONS

Blankenship, T. N., J. F. Hess, and P. G. FitzGerald. 2001. Development- and differentiation-dependent reorganization of intermediate filaments in fiber cells. *Investigative ophthalmology & visual science* 42: 735-742.
Bonomi, L et al. 1990. Evaluation of the 701 interzeag lens opacity meter. Graefe's Arch Clin Exp Ophthalmol 228(5):447-9.
Borja, D et al, 2008 Optical Power of the Isolated Human Crystalline Lens. Invest Ophthalmol Vis Sci 49(6):2541-8.
Bron, A.J., et al. "The Ageing Lens" Ophthalmologica (2000) 214(1):86-104.
Brunkener, M., and S. D. Georgatos, 1992. Membrane-binding properties of filensin, a cytoskeletal protein of the lens fiber cells. *Journal of cell science* 103 (Pt 3): 709-718.
Cenedella, R. J. 1998. Prenylation of proteins by the intact lens, *Investigative ophthalmology & visual science* 39: 1276-1280.
Croft, M. A., A. Glasser, G. Heatley, J. McDonald, T. Ebbert, N. V. Nadkarni, and P. L. Kaufman. 2006. The zonula, lens, and circumlental space in the normal iridectomized rhesus monkey eye. *Investigative ophthalmology & visual science* 47: 1087-1095.
Croft, M. A , and P. L. Kaufman. 2006. Accommodation and presbyopia: the ciliary neuromuscular view. *Ophthalmology clinics of North America* 19: 13-24, v.
Dubbelman, M., G. L. Van der Heijde, H. A. Weeber, and G. F. Vrensen. 2003. Changes in the internal structure of the human crystalline lens with age and accommodation. *Vision research* 43: 2363-2375.
Eason, R. C., H. E. Archer, S. Akhtar, and C. J. Bailey. 2002. Lipoic acid increases glucose uptake by skeletal muscles of obese-diabetic ob/ob mice. *Diabetes Obes Metab* 4: 29-35.
Egan, D., P. James, D. Cooke, and R. 0'Kennedy. 1997. Studies on the cytostatic and cytotoxic effects and mode of action of 8-nitro-7-hydroxycoumarin. *Cancer letters* 118: 201-211.
Finn, G., B. Creaven. and D. Egan, 2003. Modulation of mitogen-activated protein kinases by 6-nitro-7-hydroxycoumarin mediates apoptosis in renal carcinoma cells. *European journal of pharmacology* 481: 159-167.
Finn, G. J., B. S. Creaven, and D. A. Egan. 2004. A Study of the role of cell cycle events mediating the action of coumarin derivatives in human malignant melanoma cells. *Cancer letters* 214: 43-54.Garner, M. H., and J. R. Kuszak. 1993. Cations, oxidants, ' , cataracts. Puerto Rico health sciences journal 12: '115-122,. ILi.light as causative agents in senile I r--1 1.
Flammer J. Bebie H. 1987. Lens Opacity Meter: a new instrument to quantify lens pacity. Ophthalmologica 195(469-72.
Furuta, T S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. *Proceedings of the National Academy of Sciences of the United States of America* 96: 1193-1200.
Gail MH & You WC. 2006. A factorial trial including garlic supplements assesses effect in reducing precancerous gastric lesions. J Nutr. 136(3 Suppl):813S-815S.
Gamer, M. H., and J. Horwitz, 1994. Catalytic subunit isoforms of mammalian lens Na,K-ATPase, *Current eye research* 13: 65-77.
Garner, M. H., and Y. Kong. 1999. Lens epithelium and fiber Na,K-ATPases: distribution and localization by immunocytochemistry. *Investigative ophthalmology & visual science* 40: 2291-2298.
Garner, M. H., and J. R. Kuszak. 1993. Cations, oxidants, light as causative agents in senile cataracts. *Puerto Rico health sciences journal* 12 115-122.
Garner, M. H., and A. Spector. 1980. Selective oxidation of cysteine and rnethionine in normal and senile cataractous lenses. *Proceedings of the National Academy of Sciences of the United States of America* 77: 1274-1277.
Garner, M. H. 1994. Na,K-ATPases of the lens epithelium and fiber cell: formation of catalytic cycle intermediates and Na+: K+ exchange. *Experimental eye research* 58: 705-718.

Gilmore WJ & Kirby GM. 2004. Endoplasmic reticulum stress due to altered cellular redox status positively regulates murine hepatic CYP2A5 expression. J Pharmacol Exp Ther. 308(2):600-8. Epub Nov. 10, 2003.
Glasser, A., and M. C. Campbell. 1999. Biometric, optical and physical changes in the isolated human crystalline lens with age in relation to presbyopia. *Vision research* 39: 1991-2015.
Goulieimos, G., F. Gounari, S. Remington, S. Muller, M. Haner, U. Aebi, and S. D. Georgatos, 1996. Filensin and phakinin form a novel type of beaded intermediate filaments and coassemble de novo in cultured cells. *The Journal of cell biology* 132: 643-655.
Goulielmos, G., S. Remington, F. Schwesinger, S. D. Georgatos, and F. Gounari. 1996. Contributions of the structural domains of filensin in polymer formation and filament distribution. *Journal of cell science* 109 ( Pt 2): 447-456.
Green DR & Reed JC. 1998. Mitochondria and apoptosis. Science 281(5381): 1309-12.
Gruzman, A., A. Hidmi, J. Katzhendler, A. Haj-Yehie, and S. Sasson. 2004. Synthesis and characterization of new and potent alpha-lipoic acid derivatives. *Biorganic & medicinal chemistry* 12: 1183-1190.
Guest, P. C., H. A. Skynner, K. Salim, F. D. Tattersall, M. R. Knowles, and J. R. Atack. 2006. Detection of gender differences in rat lens proteins using 2-D-DIGE. *Proteomics* 6: 667-676.
Gurney, AM. 1994. Flash photolysis of caged compounds in *Microelectrode Techniques*, ed Ogden D, pp. 389-406.
Halhal M, et al. 2004. Iontophoresis: from the lab to the bed side. Exp Eye Res 78(3):751-57.
Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.
Heidemann, S. R., S. Kaech, R. E. Buxbaum, and A. Matus. 1999. Direct observations of the mechanical behaviors of the cytoskeleton in living fibroblasts. *The Journal of cell biology* 145: 109-122.
Hardie, R.C. 1995. Photolysis of Caged $Ca^{2+}$ Facilitates and inactivates but Does Not Directly Excite Light-Sensitive Channels in *Drosophila* Photoreceptors. The Journal of Neuroscience 15(1):899-902.
Hermans, E., M. Dubbelman, R. van der Heijde, and R. Heethaar. 2007. The shape of the human lens nucleus with accommodation. *Journal of vision* 7: 16 11-10.
Hoenders, H.J., et al. "Lens proteins and aging" J Gerontol (May 1983) 38(3):278-86.
Hofmann, M., P. Mainka, H. Tritschler, J. Fuchs, and G. Zimmer, 1995. Decrease of red cell membrane fluidity and -SH groups due to hyperglycemic conditions is counteracted by alpha-lipoic acid. *Archives of biochemistry and biophysics* 324: 85-92.
Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2008.
Ivanov, D., G. Dvoriantchikova, A. Pestova, L. Nathanson, and V. I. Shestopalov. 2005, Microarray analysis of Fiber cell maturation in the lens. *FEBS letters* 579: 1213-1219.
Janoria, K. G., S. Hariharan, D. Paturi, D. Pal, and A. K. Mitre. 2006. Biotin uptake by rabbit corneal epithelial cells: role of sodium-dependent multivitamins transporter (SMVT). *Current eye research* 31: 797-809.
Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizaide-Galvan, F. Leon-Cedeno, and J. J. Mandoki. 2001. Decrease of cyclin D1 in the human lung adenocarcincima cell line A-427 by 7-hydroxycoumarin. *Lung cancer* (Amsterdam, Netherlands) 34: 185-194.
Johansson, M., and M. Lundberg. 2007. Glutathionylation of beta-actin via a cysteinyl sulfenic acid intermediary. *BMC Biochem* 8: 26.
Jones, D. P., Y. M. Go, C. L. Anderson, T. R. Ziegler, J. M. Kinkade, Jr., and W. G. Kirlin. 2004. Cysteine/cystine couple is a newly recognized node in the circuitry for bioiogic redox signaling and control. *FASEB J* 18: 1246-1248.
Jung MY, et al. 2001. Chemopreventive allyithiopyridazine derivatives induce apoptosis in SK-Hep-1 hepatocarcinoma cells through a caspase-3-dependent mechanism. Eur J Cancer. 37(16):2104-10.

(56) References Cited

OTHER PUBLICATIONS

Jüregen, W. 2007. Synthesis and investigations of (6-hydroxy-3-oxo-3H-xanthen-9-yl)methyl derivatives. A new photoremovabie protecting group. Inaugural Dissertation at Universität Basel.

Kahn, J., P. Preis, F. Waldman, and A. Tseng, Jr. 1994. Coumarin modulates the cell-cycle progression of an MTV-EJras cell line. *Journal of cancer research and clinical oncology* 120 Suppl: S19-22.

Kao, J.P.Y. 2006, Caged Molecules: Principles and Practical Considerations. Current Protocols in Neuroscience. 6.20.1-6.20.21.

Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodation? *Nature* 285: 506-508.

Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.

Konrad, D., R. Somwar, G. Sweeney, K. Yaworsky, M. Hayashi, T. Ramial, and A. Klip. 2001. The antihyperglycemic drug alpha-lipoic acid stimulates glucose uptake via both GLUT4 translocation and GLUT4 activation: potential role of p38 mitogen-activated protein kinase in GLUT4 activation. *Diabetes* 50: 1464-1471.

Krueger, R.R., et al. "Experimental increase in accommodative potential after neodymium: yttrium-aluminum-garnet laser photodisruption of paired cadaver lenses" Ophthalmology (2001) 108(11):2122-29.

Krumdieck, C L., et al. "Mechanism of Homocysteine Toxicity on Connective Tissues: Implications for the Morbidity of Aging" J. Nutr. (2000) 130:365S-68S.

Kumar RV, et al. 1991, The nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella, 1988. An ultrastructural analysis of plasma membrane in the U18665A cataract. *Investigative ophthalmology & visual science* 29; 261-267.

Lacy, A., and R. O'Kennedy. 2004. Studies on coumarins and coumarin-related compounds to determine their therapeutic role in the treatment of cancer. *Current* pharmaceutical *design* 10:3797-3811.

Larsson, H. P., A. V. Tzingounis, H. P. Koch, and M. P. Kavanaugh. 2004. Fluorometric measurements of conformational changes in glutamate transporters. *Proceedings of the National Academy of Sciences of the United States of America*, 101: 3951-3956.

Lee V & Bundgaard H. 1992. Improved Ocular Drug Delivery with Prodrugs. In: Sloan K. ed. Produgs: Topical and Ocular Drug Delivery, vol. 53, p. 233.

Lesiński L. & Duschmalé. J. 2006. Flash Photolysis in Praktikum "Physikalische Chemie" pp. 1-8.

Li, L., J. Lim, M. D. Jacobs, J. Kistler, and P. J. Donaldson. 2007. Regional differences in cystine accumulation point to a sutural delivery pathway to the lens core. *Investigative ophthalmology & visual science* 48: 1253-1260.

Lim, J., Y. C. Lam, J. Kistler, and P. J. Donaldson. 2005. Molecular characterization of the cystine/glutamate exchanger and the excitatory amino acid transporters in the rat lens. *Investigative ophthalmology & visual science* 46: 2869-2877.

Lim, J., L. Li, M. D. Jacobs, J. Kistler, and P. J. Donaldson. 2007. Mapping of glutathione and its precursor amino acids reveals a role for GLYT2 in glycine uptake in the lens core, *Investigative ophthalmology & visual science* 48: 5142-5151.

Lindsey Rose, K. M., R. G. Gourdie, A. R. Prescott, R. A. Quinlan. R. K. Crouch, and K. L. Schey. 2006. The C terminus of lens aquaporin 0 interacts with the cytoskeletal proteins D filensin and CP49. *Investigative ophthalmology & visual science* 47: 1562-1570.

Liu H, et al. 1997. Endoplasmic reticulum chaperones GRP78 and caireticulin prevent oxidative stress, Ca2+ disturbances, and cell death in renal epithelial cells. J Biol Chem. 272(35):21751-9.

Liu, J., E. Head, A. M. Gharib, W. Yuan, R. I ingersoll, T. M. Hagen, C. W. Cotrnan, and B. N. Ames. 2002. Memory loss in old rats is associated with brain mitachondrial decay and RNA/DNA oxidation: partial reversal by feeding acetyl-L-carnitine and/or R-alpha-lipoic acid. *Proceedings of the National Academy of Sciences of the United States of America* 99: 2356-2361.

Lopez-Gonzalez, J. S., H. Prado-Garcia, D. Aguilar-Cazares, J, A. Molina-Guarneros, J. Morales-Fuentes, and J. J. Mandoki. 2004. Apoptosis and cell cycle disturbances induced by coumarin and 7-hydroxycoumarin on human lung carcinoma cell lines. *Lung cancer* (Amsterdam, Netherlands) 43: 275-283.

Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. *Mol Pharm* 3: 329-339.

Maitre, I., E. Serbinova, H. J. Tritschler, and L. Packer. 1996. Stereospecific effects of R-lipoic acid on buthionine sulfoximine-induced cataract formation in newborn rats. *Biochemical and biophysical research communications* 221: 422-429.

Maitre, I., E. Serbinova, H. Trischler, and L. Packer, 1995. Alpha-lipoic acid prevents buthionine sulfoximine-induced cataract formation in newborn rats. *Free radical biology & medicine* 18: 823-829.

Manns, F., J. M. Parel, D. Denham, C. Billotte, N. Ziebarth, D. Borja, V. Fernandez, M. Aly, E. Arrieta, A. Ho, and B. Holden. 2007. Optomechanicai response of human and monkey lenses in a lens stretcher. *Investigative ophthalmology & visual science* 48: 3260-3268.

Merdes, A., M. Brunkener, H. Horstmann, and S. D. Georgatos. 1991. Filensin: a new vimentin-binding, polymerization-competent, and membrane-associated protein of the lens fiber cell. *The Journal of cell biology* 115: 397-410.

Merdes, A., F. Gounari, and S. D. Georgatos. 1993. The 47-kD lens-specific protein phakinin is a tailless intermediate filament protein and an assembly partner of filensin. *The Journal of cell biology* 123: 1507-1516. i.

Moffat, B.A., et al. "Age-related Changes in the Kinetics of Water Transport in Normal Human Lenses" Exp. Eye Res. (1999) 69(6):663-69.

Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. *Archives of biochemistry and biophysics* 397: 384-391.

Muchowski, P. J., M. M. Valdez, and J. I. Clark. 1999. AlphaB-crystallin selectively targets intermediate filament proteins during thermal stress. *Investigative ophthalmology & visual science* 40: 951-958.

Musk SR, et al. 1997. Cytotoxicity and genotoxicity of diallyl sulfide arid diallyl disulfide towards Chinese hamster ovary cells. Food Chem Toxicol. 35(3-4):379-85.

Newell. 1996. Ophthalmology: Principles and Concepts St. Louis: Mosby-Year Book St. Louis, p. 83.

Obrosova I, et al. 1998. Diabetes-induced changes in lens antioxidant status, glucose utilization and energy metabolism: effect of DL-alpha-lipoic acid. Diabetologia 41(12):1442-50.

Ong, M. D., D. M. Payne, and M. H. Garner, 2003. Differential protein expression in lens epithelial whole-mounts and lens epithelial cell cultures. *Experimental eye research* 77: 35-49.

Pau, H., and J. Kranz. 1991. The increasing sclerosis of the human lens with age and its relevance to accommodation and presbyopia. *Graefe's archive for clinical and experimental ophthalmology=Albrecht von Graefes Archiv fur klinische and experimentelle Ophthalmologie* 229: 294-296.

Petit PX, et al. 1995. Alterations in mitochondrial structure and function are early events of dexamethasone-induced thymocyte apoptosis. J Cell Biol. 130(1)157-67.

Phelps-Brown, N.A., et al. "Nutritional supplements and eye" Eye (1998) 12:127-33.

Pierscionek, B. K. 1995, Age-related response of human lenses to stretching forces. *Experimental eye research* 60: 325-332.

Reddy, N. S., K. Cumireddy, M. R. Mallireddigari, S. C. Cosenza. P. Venkatapuram, S. C. Bell, E. P. Reddy, and M. V. Reddy. 2005. Novel coumarin-3-(N-aryl)carboxamides arrest breast cancer cell growth by inhibiting ErB-2 and ERK1. *Bioorgarnic & medicinal chemistry* 13:3141-3147.

Salvioli S, et al. 1997. JC-1, but not DiOC6(3) or rhodamine 123, is a reliable fluorescent probe to assess delta psi changes in intact cells:

(56) References Cited

OTHER PUBLICATIONS implications for studies on mitochondrial functionality during apoptosis. FEBS Lett. 411(1):77-82.
Sandilands, A., A. R. Prescott, A. M. Hutcheson, R. A. Quinlan, J. T. Casselman and P. G. FitzGerald. 1995. Filensin is proteolyticaily processed during lens fiber cell differentiation by multiple independent pathways. *European journal of cell biology* 67: 238-253.
Sarraf D & Lee DA. 1994. The Role of Iontophoresis in Ocular Drug Delivery. J Ocul 144 Pharmacol 10(1):69-81.
Sato, H., M. Tamba, K. Kuriyama-Matsumura, S. Okuno, and S. Bannai. 2000. Molecular cloning and expression of human xCT, the light chain of amino acid transport system *xc*. *Antioxid Redox Signal* 2: 665-671.
Sato, H., M. Tamba, T. Ishii, and S. Bannai. 1999. Cloning and expression of a plasma membrane cystine/glutamate exchange transporter composed of two distinct proteins, *The Journal of biological chemistry* 274: 11455-11458.
Sato, H., A. Shiiya, M. Kimata, K. Maebara, M. Tamba, Y. Sakakura, N. Makino, F. Sugiyama, K. Yagami, T. Moriguchi, S. Takahashi and S. Bannai. 2005. Redox imbalance in cystine/glutamate transporter-deficient mice, *The Journal of biological chemistry* 280: 37423-37429.
Schonheit, K., L. Gille, and H. Nohl. 1995. Effect of alpha-lipoic acid and dihydrolipoic acid on ischemia/reperfusion injury of the heart and heart mitochondria. *Biochimica et biophysica acta* 1271: 335-342.
Senda, N. 2006. Synthesis and Photochemical Properties of a New Water-Soluble Coumarin, Designed as a Chromophore for Highly Water-Soluble and Photolabiie Protecting Group. Bull. Chem. Soc. Jpn. vol. 79, No. 11, 1753-1757.
Shembekar, V. R., Y. Chen, B. K. Carpenter, and G P. Hess. 2005. A protecting group for carboxylic acids that can be photolyzed by visible light. *Biochemistry* 44: 7107-7114.
Spector, A., et al, "Thioredoxin fragment 31-36 is reduced by dihydroliooamide and reduces oxidized protein" Biochem Biophys Res Commun (Jan. 1988) 150(1)156-62.
Strenk, S. A., L. M. Strenk, J. L. Semmlow, and J. K. DeMarco. 2004. Magnetic resonance imaging study of the effects of age and accommodation on the human lens cross-sectional area. *Investigative ophthalmology & visual science* 45: 539-545.
Sundaram SG & Milner JA. 1996. Diallyl disulfide suppresses the growth of human colon tumor cell xenografts in athymic nude mice. J Nutr. 126(5):1355-61.
Sweeney, M. H., and R. J. Truscott. 1998. An impediment to glutathione diffusion in older normal human lenses: a possible precondition for nuclear cataract. *Experimental eye research* 67: 587-595.
Tamm, E., E. Lutjen-Drecoll, W. Jungkunz, and J. W. Rohen. 1991. Posterior attachment of ciliary muscle in young, accommodating old, presbyopic monkeys. *Investigative ophthalmology & visual science* 32: 1678-1692.
Tamm, E., E. Tamm, and J. W. Rohen. 1992. Age-related changes of the human ciliary muscle. A quantitative morphometric study. *Mechanisms of ageing and development* 62: 209-221.
Truscott, R. J. 2000. Age-related nuclear cataract: a lens transport problem. *Ophthalmic research* 32: 185-194.
Wang, C. J., Y. J. Hsieh, C. Y. Chu, Y. L. Lin, and T. H. Tseng, 2002. Inhibition of cell cycle progression in human leukemia HL-60 cells by esculetin, *Cancer letters* 183: 163-168.
Wang, S. J., and H. H. Chen. 2007. Presynaptic mechanisms underlying the alpha-iipoic acid facilitation of glutamate exocytosis in rat cerebral cortex nerve terminate. *Neurochernistey international* 50: 51-60.
Weeber, HA et al. 2007. Stiffness gradient in the crystalline lens. Graefes Arch Clin Exp Ophthalmol 245(9):1357-66.
Widornska, J., M. Raguz, J. Dillon, E. R. Gaillard, and W. K Subczynski. 2007. Physical properties of the lipid bilayer membrane made of calf lens lipids: EPR spin labeling studies, *Biochimica et biophysica acta* 1768: 1454-1465..
Wieboidt, R. et al. 1994. Photolabile precursors of glutamate: Synthesis, photochemical properties, and activation of glutamate receptors on a microsecond time scale. Proc. Natl. Acad. Sci, 91:8752-8756.
Willner I & Zahavy E. 1994. Activation of Glutathione Reducase by Light: A Novel Approach to Design Redox Photo-Enzymes, Angew Chem Int Ed Engl 33(5):581-83.
Yin MC, et al. 2002. Nonenzymatic antioxidant activity of four organosulfur compounds derived from garlic. J Agric Food Chem. 50(21):6143-7.
Yu, N. T., D. C. DeNagei, P. L. Pruett, and J. F. Kuck, Jr. 1935. Disulfide bond formation in the eye lens. *Proceedings of the National Academy of Sciences of the United States of America* 82: 7965-7968.
Zhao, Y., Q. Zheng, K. Dakin, K. Xu, M. L. Martinez, and W. H. Li. New caged coumarin fluorophores with extraordinary uncaging cross sections suitable for biological imaging applications. *Journal of the American Chemical Society* 126: 4653-4663.
Zivkovic, D. 2007. Investigations on 2,7-diamino-9-fluorenol photochemistry. Inaugural Dissertation at Universität Basel.
Ip C, Ganther HE. 1992. Comparison of selenium and sulfur analogs in cancer prevention, Carcinogenesis. 13(7): 1167-70.
Aloisi et al. 1948. Glycerylphosphorylcholine and Choline Glycerophosphate. Biochemical Journal. vol. 43, pp. 157-161; p. 157, col. 1, para 2-3; col. 2, para 1; p. 158, col. 1, para 4.
Gilbert, Basic Concepts in Biochemistry USA. McGraw Hill 2000 p. 184.
Jablonski et al. Plant Physiology 1978 61:221-225.
Ng et al. Experimental Eye Research 1986 43:477-489.
Morris Jr. Recent advances in arginine metabolism; roles and regulation of the arginases. British Journal of Pharmacology, E-Pub Jun. 5, 2009, 157(6):922-930.
PubChem Compound Summary CID 863 lipoamide (Seo. 16, 2004) (Retrieved from the internet Nov. 13, 2010; http://pubchem.ncbi.nlm.nih.gov/summary/summary.cgi?cid=863.
Salceda, et al. L-arginine uptake in normal and diabetic rat retina and retinal pigment epithelium. Neurochem Res., 2008, 33(8):1541-1545.
Stuehr et al. Nw-Hydroxy-L-arginine is an intermediate in the Biosynthesis of nitric Oxide from L-Arginine. The Journal of Biological Chemistry 1991, 266(10):6259-6263.
Trusoott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.
JP Office Action in JP2007-537922.
The Extended Search Report corresponding to the European application No. 09825441.0.
The Extended European Search Report received in the related European application No. 10790038.3.
Office Communication received in the related Mexican Application No. MX/a/2007/004775.

DITHIOL COMPOUNDS, DERIVATIVES, AND TREATMENT OF PRESBYOPIA

CROSS-REFERENCES TO RELATED APPLICATIONS

This application claims the benefit of U.S. Provisional Patent Application 61/033,870 filed Mar. 5, 2008, U.S. Provisional Patent Application 61/060,487 filed Jun. 11, 2008, and U.S. Provisional Patent Application 61/077,186 filed Jul. 1, 2008. Each of these is incorporated herein by reference in its entirety.

BACKGROUND OF THE INVENTION

As we age, our lenses undergo physiological changes that make it more difficult to focus on near objects. That is why nearly everyone requires reading glasses, even as early as age 35-40. The ability of the eye to change focal power, also known as accommodative amplitude, decreases significantly with age. The accommodative amplitude is 20 diopters in children and young adults, but it decreases to 10 diopters by age 25 and to ≤1 diopter by age 60. The age-related inability to focus on near objects is called presbyopia. All of us will develop presbyopia and will require corrective lenses unless a new treatment is found.

Both presbyopia and cataract are age-related and may share common etiologies such as lens growth, oxidative stress, and/or disulfide bond formation.

There is a need for agents, compositions, and methods for combating ocular disease, including presbyopia and/or cataract.

BRIEF SUMMARY OF THE INVENTION

In one embodiment, a method of treating presbyopia comprises administering an agent including at least two components independently selected from a sulfur atom, a selenium atom, and a sulfonic group. In one embodiment, at least one of the two components is selenium. The agent can be a five- or six-membered heterocycle or a non-cyclical compound.

In another embodiment, the agent has a formula of 6-A, 6-B, 6-C, 6-D, or 6-E. In another embodiment, the agent has the formula 6-A. In another embodiment, the agent has a formula 6-D or 5-E. In another embodiment, the agent has a formula 6-NC or 5-NC. In yet another embodiment, the agent has a formula 5-A or 5-B. In another embodiment, the agent has the formula NC.

Each of X and Y can be sulfur, selenium, or a sulfonic group. In one embodiment, X and Y are both sulfur. In another embodiment, one of X and Y is sulfur, and the other is sulfur or selenium.

Each R group is independently selected from the group consisting of: —H, —OH, —OAc, —OR, —SR, —$CO_2R$, an electron withdrawing group, and a linear or branched $C_{1-18}$ alkane or alkene optionally substituted by one or more substituents selected from the group consisting of ether, ester, carboxylic acid, phosphate, amide, and amine groups. In another embodiment, at least one R group is —OH or —OAc.

In yet another embodiment, at least one R group is a $C_{2-10}$ alkane or $C_{10-18}$ alkene. In another embodiment, at least one R group is —$(CH_2)_{2-10}NH_2$. In another embodiment, at least one R group is —$(CH_2)_{2-10}CO_2H$.

In one embodiment, the agent is one of the following or a derivative thereof: lipoic acid; cystine; 3,6-dihydro-1,2-dithiine; 3,4-dihydro-1,2-dithiine; 3-vinyl-[4H]-1,2-dithiine; diallyl disulfide; diallyl trisulfide; 3-prop-2-enylsulfinylsulfanylprop-1-ene; 1,2-dithiane; 6-((4R,5R)-4,5-dihydroxy-1,2-dithian-4-yl)hexanoate; (4R,5R)-5-hydroxy-1,2-dithian-4-yl acetate; (4R,5R)-1,2-dithian-4,5-diyl diacetate; or trans-4,5-dihydroxy-1,2-dithiane; or dithiothreitol.

In another embodiment, the agents are employed for pharmaceutical formulations and/or methods of treating ocular disease, e.g., presbyopia or cataract.

BRIEF DESCRIPTION OF THE FIGURES

FIG. 3 depicts the average opacity (opacimetry) of an untreated human lens as a function of age in years. Bonomi, L et al. 1990. Evaluation of the 701 interzeag lens opacity meter. Graefe's Arch Clin Exp Opthalmol 228(5):447-9. Lens opacity was measured in 73 healthy subjects between 10 and 76 years of age without slit-lamp evidence of cataract and with a visual acuity of 20/20. These subjects were classified into ten age groups. This study was carried out using the Interzeag Opacity Meter according to the procedure described by Flammer and Bebies (Flammer J, Bebie H. 1987. Lens Opacity Meter: a new instrument to quantify lens opacity. Opthalmologica 195(2):69-72) and following the suggestions of the operating manual for the instrument.

FIG. 5 depicts a scattergram of the percent of the total protein SH groups in disulfide bonds. Free SH groups were alkylated with 4-acetamido-4'-maleimidylstilbene-2,2'-sulfonic acid (c, 1 μM, 5 μM, 9.6 μM, 50 μM, 96 μM) or 7-diethylamino-3-(4'maleimidylphenyl)-4-methyl coumarin (500 μM, and 500 μM c). Following removal of the first alkylating agent, the S—S bonds were reduced and alkylated with fluorescein-5-maleimide. Absorption spectra were used to calculated total protein (A280 nm), free protein SH (A322 or A384), and protein SS (A490) using the appropriate extinction coefficients. The symbol ‡ indicates statistically significant difference of mean with mean of control (c, p≤0.05). The symbol ** indicates means of 500 μM lipoic acid and the 500 μM control were significantly different from each other (p=0.027).

DETAILED DESCRIPTION OF THE INVENTION

Agents, compositions, and methods are provided that can prevent, reduce, reverse, and/or slow the rate of lens growth, oxidative damage, and/or disulfide bond formation. These agents, compositions, and methods may thus effectively prevent or treat presbyopia and/or cataract.

The agents described herein are dithiol compounds or dithiol derivatives. The dithiol compounds and dithiol derivatives are referred collectively herein as agents. Dithiol compounds contain at least two sulfur atoms, preferably exactly two sulfur atoms, while dithiol derivatives include a selenium or sulfonic group in place of one or more sulfur atoms of a dithiol compound. Thus, in one embodiment, the agent has at least two components, each independently selected from a sulfur atom, a selenium atom, and a sulfonic group. In another embodiment, the agent has at least two components, each independently selected from a sulfur atom and a selenium atom. The agents can be on the backbone and/or the substituents of the compound.

The agents can be cyclical, e.g. a five- or six-membered heterocycle, or non-cyclical. Exemplary five-membered heterocycles (designated by Formula 5) include, but are not limited to:

Formula 5-A

Formula 5-B

Exemplary six-membered heterocycles (designated by Formula 6) include, but are not limited to:

Formula 6-A

Formula 6-B

Formula 6-C

Formula 6-D

Formula 6-E

Exemplary non-cyclical agents (designated by NC) include, but are not limited to:

Formula 5-NC

Formula 6-NC

Formula NC

The agents can be classified in various ways. For example, the agent can be encompassed by any one of the following classification groups:
  5-A, 5-B, 6-A, 6-B, 6-C, 6-D, and 6-E: cyclical
  5-NC, 6-NC, and NC: non-cyclical
  5-A, 5-B, and 5-NC: 5-membered
  5-A and 5-B: 5-membered cyclical
  6-A, 6-B, 6-C, 6-D, 6-E, and 6-NC: 6-membered
  6-A, 6-B, 6-C, 6-D, and 6-E: 6-membered cyclical
  5-A and 5-NC: potential hydrogenation pair
  6-A and 6-NC: potential hydrogenation pair
  5-NC and 6-NC: potential hydrogenation products
  5-A, 6-A, 6-D, and 6-E: adjacent thiols
  5-A and 6-A: adjacent thiols, saturated ring
  6-A, 6-D, and 6-E: adjacent thiols, 6-membered cyclical
  5-B, 6-B, and 6-C: non-adjacent thiols
  5-B and 6-B: 1,3 thiols
  6-A, 6-B, and 6-C: dithanes
  6-D and 6-E: dithiines
or the agents can be classified by any individual formula.

For each of the agents, X and Y are independently selected from a sulfur atom, a selenium atom, and a sulfonic group. Preferably, at least one of X and Y is sulfur. In one embodiment, X and Y are both sulfur. In another embodiment, one of X and Y is sulfur, and the other is sulfur or selenium. In yet another embodiment, one of X and Y is sulfur, and the other is selenium. In one embodiment, the agent is a seleno derivative where at least one of X and Y is selenium. Without being bound by theory, it is believed that the selenium atom advantageously helps to overcome redox potential.

Each R group is independently selected from —H, —OH, —OAc, —OR, —SR, —CO$_2$R, an electron withdrawing group, and a linear or branched C$_{1-18}$ alkane or alkene optionally substituted by one or more ether, ester, carboxylic acid, phosphate, amide, and/or amine groups. In another embodiment, each R group is independently —H, —OH, —OAc, —CO$_2$CH$_3$, or a linear C$_{1-18}$ alkane or alkene optionally having a distal terminal that is —COOH, —NH$_2$, —CO$_2$CH$_3$, or —CO$_2$CH$_2$CH$_3$.

In one embodiment, various agents can be prepared by altering the placement of a particular R group. Any particular R group can be attached, for example, to a carbon adjacent to a thiol group (sulfur atom) or thiol derivative (e.g., selenium or sulfonic group). R$_1$, R$_2$, R$_7$, R$_8$, R$_9$, R$_{10}$, R$_{11}$, R$_{12}$, R$_{13}$, and R$_{14}$ represent such thiol-adjacent positions. In another embodiment, an R group can be attached to a carbon not adjacent to a thiol group or thiol derivative. R$_3$, R$_4$, R$_5$, and R$_6$ represent such non-adjacent positions. In yet another embodiment, an R group can be attached directly to a thiol group or thiol derivative. R$_{15}$, R$_{16}$, R$_{17}$, and R$_{18}$ represent such direct thiol attachments.

In one embodiment, one, two, or more R groups are —H. In some embodiments of Formula 5-NC and 6-NC, both of R$_{15}$ and R$_{16}$ are —H.

In one embodiment, one, two, or more R groups are —OH.

In another embodiment, one, two, or more R groups are —OAc. Without being bound by theory, the addition of an acetate ester (—OAc) is believed to improve corneal permeability, which is especially beneficial for the treatment of presbyopia.

In yet another embodiment, each R group is independently —H, —OH, —OAc, or —CH$_3$. In another embodiment, one R group is a chain substituent, and the remaining R groups are independently —H, —OH, —OAc, or —CH$_3$.

In one embodiment, the agent has the structure of Formula 6-A:

wherein each of R$_1$, R$_2$, R$_7$, and R$_8$ is —H; and

R$_3$, R$_4$, R$_5$, and R$_6$ are independently selected from —H, —OH, and —OAc.

In another embodiment, one, two, or more R groups are —CO$_2$R. In another embodiment, one, two, or more R groups are —OR. In particular embodiments, the R of —CO$_2$R or —OR is a lower alkyl group having 1-8 carbons. In one embodiment, —CO$_2$R is —CO$_2$CH$_3$.

In one embodiment, the agent includes a C$_{1-18}$ alkane or alkene, which are collectively referred to herein as chain substituents. The agent can be modified by altering the length of the chain substituent(s). Without being bound by theory, longer chains are believed to render the compound more hydrophobic, more lipid soluble, and thus more easily transported across the cell membrane. The length of the chain is limited by the lipid membrane width; a chain longer than the membrane width is likely to cause saponification. Shorter chains, on the other hand, and other similarly small substituents such as —OH and —CO$_2$CH$_3$, may be useful for preparing agents that are active in the cytosol and do not require membrane permeability. Substituent size and its concomitant effect on solubility also affect formulation considerations. For example, a hydrophobic drug may be more difficult to formulate as an administratable solution, but it may be more easily formulated for sustained release delivery systems.

In one embodiment, the agent includes a linear C$_{1-18}$ alkane or alkene, which are collectively referred to herein as linear substituents. Without being bound by theory, linear substituents are more commonly found in natural compounds, so agents including linear substituents may be better tolerated by the body. However, branched substituents may also be used. The linear substituent can be, for example, attached to a carbon adjacent to a thiol group (sulfur atom) or thiol derivative (e.g., selenium or sulfonic group). In other words, one or more of R$_1$, R$_2$, R$_7$, R$_8$, R$_9$, R$_{10}$, R$_{11}$, R$_{12}$, R$_{13}$, and R$_{14}$ can be a linear substituent. In another embodiment, one or more of R$_3$, R$_4$, R$_5$, and R$_6$ can be a linear substituent.

In one embodiment, a chain substituent includes an ether, ester, carboxylic acid, phosphate, and/or amine group at the distal terminal of a chain. In one embodiment, the distal terminal is a carboxylic acid or an amine. In another embodiment, one, two, or more R groups are —(CH$_2$)$_{2-10}$CO$_2$H or —(CH$_2$)$_{2-10}$NH$_2$. Without being bound by theory, it is believed that carboxylic acid and amine terminals provide attachment points for natural amino acids to form peptide amide bonds. For example, the carboxylic acid terminal of exemplary agent lipoic acid is often covalently attached to the amine lysine side chain of the active mitochondrial enzyme. The mitochondrial functionality of lipoic acid is discussed in further detail below.

In another embodiment, the distal terminal of a chain substituent is an ester, e.g., methyl or ethyl ester. In one embodiment, one, two, or more R groups are —(CH$_2$)$_{2-10}$CO$_2$CH$_3$ or —(CH$_2$)$_{2-10}$CO$_2$CH$_2$CH$_3$. Without being bound by theory, esterification is one way to modify the delivery of the pharmaceutical agent since the agent is inhibited from entering the cell until the ester is broken, e.g., by naturally occurring esterases. In this way, an esterified agent can serve as a prodrug that can be converted to an active form.

In one embodiment, the linear substituent is a linear C$_{1-18}$, C$_{2-12}$, C$_{2-10}$, C$_{2-8}$, C$_{2-6}$, C$_{4-6}$, C$_{5-6}$, or C$_5$ alkane. Exemplary agents including a linear alkane substituent are provided in the table below. The remaining undefined R groups are independently —H, —OH, —OAc, or —CH$_3$.

TABLE 1

| Formula | X, Y | R |
|---|---|---|
| 5-A;<br>5-NC; or<br>6-B | X is S and Y is S | R$_1$ or R$_3$ is:<br>—(CH$_2$)$_{3-10}$CO$_2$H;<br>—(CH$_2$)$_{3-10}$CO$_2$CH$_3$; or<br>—(CH$_2$)$_{3-10}$CO$_2$CH$_2$CH$_3$ |
| 5-A;<br>5-NC; or<br>6-B | X is S and Y is S;<br>X is S and Y is Se; or<br>X is Se and Y is S | R$_1$ or R$_3$ is:<br>—(CH$_2$)$_{1-2}$CO$_2$H;<br>—(CH$_2$)$_{1-2}$CO$_2$CH$_3$;<br>—(CH$_2$)$_{1-2}$CO$_2$CH$_2$CH$_3$; or<br>—(CH$_2$)$_{2-10}$NH$_2$ |
| 5-A<br>5-NC<br>6-B | X is S and Y is Se; or<br>X is Se and Y is S | R$_1$ or R$_3$ is:<br>—(CH$_2$)$_{3-10}$CO$_2$H;<br>—(CH$_2$)$_{3-10}$CO$_2$CH$_3$; or<br>—(CH$_2$)$_{3-10}$CO$_2$CH$_2$CH$_3$ |
| 6A<br>6-NC | X is S and Y is S;<br>X is S and Y is Se; or<br>X is Se and Y is S | R$_1$ or R$_3$ is:<br>—(CH$_2$)$_{2-10}$CO$_2$H;<br>—(CH$_2$)$_{2-10}$NH$_2$;<br>—(CH$_2$)$_{2-10}$CO$_2$CH$_3$; or<br>—(CH$_2$)$_{2-10}$CO$_2$CH$_2$CH$_3$ |

TABLE 1-continued

| Formula | X, Y | R |
| --- | --- | --- |
| 5-B | X is S and Y is S; <br> X is S and Y is Se; or <br> X is Se and Y is S | $R_1$ or $R_9$ is: <br> —$(CH_2)_{2-10}CO_2H$; <br> —$(CH_2)_{2-10}NH_2$; <br> —$(CH_2)_{2-10}CO_2CH_3$; or <br> —$(CH_2)_{2-10}CO_2CH_2CH_3$ |
| 6-D <br> 6-E | X is S and Y is S; <br> X is S and Y is Se; or <br> X is Se and Y is S | $R_1$, $R_3$, $R_5$, or $R_7$ is: <br> —$(CH_2)_{2-10}CO_2H$; <br> —$(CH_2)_{2-10}NH_2$; <br> —$(CH_2)_{2-10}CO_2CH_3$; or <br> —$(CH_2)_{2-10}CO_2CH_2CH_3$ |

Exemplary agent lipoic acid and some derivatives thereof include a linear alkane with a carboxylic acid terminal:

Lipoic acid

Dihydrolipoic acid

In one embodiment, the agent is lipoic acid (5-(1,2-dithiolan-3-yl)pentanoic acid), particularly alpha lipoic acid. In another embodiment, the agent is a lipoic acid derivative. Preferred lipoic acid derivatives do not interfere with the natural cellular mechanisms utilizing lipoic acid and/or dihydrolipoic acid. The agents described herein include those having relatively minor modifications to lipoic acid (e.g., altering chain length, replacing a sulfur atom with selenium) such that naturally occurring mitochondrial mechanisms can utilize either lipoic acid or the derivative. Agents having minor modifications may be relatively substitutable for lipoic acid and do not interfere with mitochondrial activity. Thus, in one embodiment, the agent functionally mimics lipoic acid in terms of redox activity and/or mitochondrial activity, but is not structurally identical to lipoic acid. Other agents include those having more major modifications to lipoic acid (e.g., altering chain placement). Such major modifications may render the agent unrecognizable to the mitochondria, thus avoiding interference with cellular mechanisms. In this way, both minor and major modifications can avoid mitochondrial interference. Mitochondrial interference, or the lack thereof, can be verified by in vitro testing according to methods known in the art such as, for example, a JC-1 Mitochondrial Membrane Potential Assay Kit (Cell Tech. Inc.). One of ordinary skill in the art could balance the strength of the reducing agent, which is believed to be responsible for the therapeutic effect, against mitochondrial interference, which might cause adverse effects. Exemplary lipoic acid derivatives include, but are not limited to: 5-(1,2-thiaselenolan-5-yl)pentanoic acid and 5-(1,2-thiaselenolan-3-yl)pentanoic acid.

In another embodiment, the linear substituent is a linear $C_{1-18}$, $C_{1-8}$, $C_{5-15}$, $C_{10-18}$, or $C_{10-16}$, or $C_{12-14}$ alkene. The alkene chain can have one, two, three, or more double bonds. Without being bound by theory, linear alkenes of relatively longer length, e.g., $C_{10-18}$, particularly those including a carboxylic acid or ester group, may exhibit advantageous properties similar to a fatty acid group.

Alkenes, including those of shorter lengths, are also useful, especially for embodiments of Formula NC. For example, in one embodiment, each of $R_{17}$ and $R_{18}$ is independently selected from $C_{2-8}$, $C_{2-6}$, $C_{3-6}$, $C_{3-5}$, or $C_3$ alkenes. In another embodiment of Formula NC, $R_{17}$ and/or $R_{18}$ is an —$SC_{2-8}$ alkene.

A chain substituent can include more than one ether, ester, carboxylic acid, phosphate, or amine substituent. For example, one exemplary agent is cystine (3,3'-disulanedylbis (2-aminopropanoic acid)), which includes both carboxylic acid and amine substituents. In one embodiment, the agent is cystine or a derivative thereof such as the exemplary derivative shown below:

cystine

In another embodiment, R is an electron withdrawing group, which can decrease the pKa of the agent. Electron withdrawing groups include, but are not limited to: halogens (e.g., F, Cl), nitriles (CN), carboxylic acids (COOH), and carbonyls (CO).

In one embodiment, the agent is an allium oil antioxidant or a derivative thereof. Allium oil antioxidants are advantageously natural, nontoxic, and lipid soluble. Some have been studied as potential cytostatic agents for the treatment of atherlerosclerosis, cancer, etc. Without being bound be theory, the cytostatic properties may also provide advantageous efficacy in the context of ocular diseases caused by lens growth, including presbyopia and cataract.

One class of allium oil antioxidants is the dithiines. Exemplary dithiines include, but are not limited to:

3,6-dihydro-1,2-dithiine

-continued 3,4-dihydro-1,2-dithiine   3-vinyl-[4H]-1,2-dithiine

Other allium oil antioxidants include, but are not limited to:

Diallyl disulfide (allitin)

Diallyl trisulfide (allitridin)

3-prop-2-enylsulfinylsulfanylprop-1-ene (allicin)

In another embodiment, the agent can be a dithiane or a derivative thereof. Without being bound by theory, it is believed that dithianes increase cellular non-protein SH, a primary objective in the treatment of presbyopia. Exemplary dithianes include, but are not limited to:

6-((4R,5R)-4,5-dihydroxy-1,2-dithian-4-yl) hexanoate

(4R,5R)-5-hydroxy-1,2-dithian-4-yl-acetate

-continued (4R,5R)-1,2-dithian-4,5-diyl-diacetate

In one embodiment, the agent is a derivative of dithiothreitol (DTT) such as trans-4,5-dihydroxy-1,2-dithiane, also referred to herein as "non-lethal DTT":

Trans-4,5-dihydroxy-1,2-dithiane (Non-lethal DTT)   Dithiothreitol (DTT)

Both DTT and non-lethal DTT possess potent antioxidant properties, but non-lethal DTT possesses the further advantage of reduced toxicity thereby being more favorable for use in in vivo settings.

The active agent can be administered as a racemate or as an enantiomer. For example, lipoic acid and its derivatives are preferably administered to include the R form; cystine and its derivatives are preferably administered to include the L form. Synthetic methods to yield a racemate may be less expensive than stereo-specific processes including isolation/purification steps. On the other hand, administering a single enantiomer can lower the therapeutically effective amount, thus decreasing toxicity effects.

The agents described herein are preferably reducing agents. For example, the agents can possess a redox potential $E_0'(V)$ of about −0.01 to about −1.0, about −0.1 to about −0.5, about −0.2 to about −0.4, or about −0.3. The agents described herein preferably exhibit an acceptable toxicity profile, e.g., a median lethal dose ($LD_{50}$) of at least 10 μM, at least 20 μM, at least 40 μM, or at least 1 mM. Toxicity can be assessed by any method known in the art such as, for example, viability of human umbilical vein endothelial cells (HUVEC, first passage) using the MultiTox-Fluor assay (Promega) or Live/Dead® assay (Invitrogen). Of course, agents selected as pharmaceutical agents for the treatment of presbyopia should exhibit both antioxidant efficacy (reducing power) as well as a desirable safety profile (low toxicity). Accordingly, in one embodiment, a screening method is provided whereby dithiol compounds or derivatives are tested for reducing power and/or toxicity. In another embodiment, a method includes screening dithiol compounds or dithiol derivatives for their ability to increase lens elasticity either in vitro or in vivo.

The agents described herein preferably exhibit favorable membrane permeability, specifically corneal permeability. Corneal penetration can be measured by methods known in the art, such as, for example, those disclosed in Kim et al. (2005) "Aqueous penetration and biological activity of moxifloxacin 0.5% ophthalmic solution and gatifloxacin 0.3% solution in cataract surgery patients" Opthalmology 112(11): 1992-96. In one embodiment, the agent enters the lens epithelial cells using a naturally occurring transport mechanism.

For example, lipoic acid and cystine enter lens cells via specific plasma membrane symporters and antiporters. By using lipoic acid, cystine, or derivatives thereof, one can utilize a naturally occurring transport mechanism to deliver the agents to the lens cells.

In another embodiment, a pharmaceutical composition includes an agent as described herein and a pharmaceutically acceptable carrier. The pharmaceutical composition may also contain one or more excipients as is well known in the art of pharmaceutical formulary. In one embodiment, the pharmaceutical composition is formulated for ocular use. That is, the pharmaceutically acceptable carrier and/or other excipients are selected to be compatible with, and suitable for, ocular use. Such carriers and excipients are well known in the art. The excipients may also be selected and/or formulated to improve the solubility of the compound. For example, the pharmaceutical composition can include one or more of emulsifiers, buffers, salts, preservatives, lubricants, polymers, solvents, and other known excipients for ocular pharmaceutical formulations. In one embodiment, the pharmaceutical composition includes an emulsifier and a buffered carrier such as Polysorbate 80 in HBSS (Hank's Balanced Salt Solution).

In another embodiment, the agents are employed in a method for treating ocular disease, e.g., presbyopia, by administering an effective amount of the agent. In another embodiment, the agents are employed in a method for preventing or reversing oxidative damage to cells, e.g., lens cells. The agents can be applied to lenses or cells in vitro or in vivo.

The term "effective amount" means an amount that is capable of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

Figure 1:
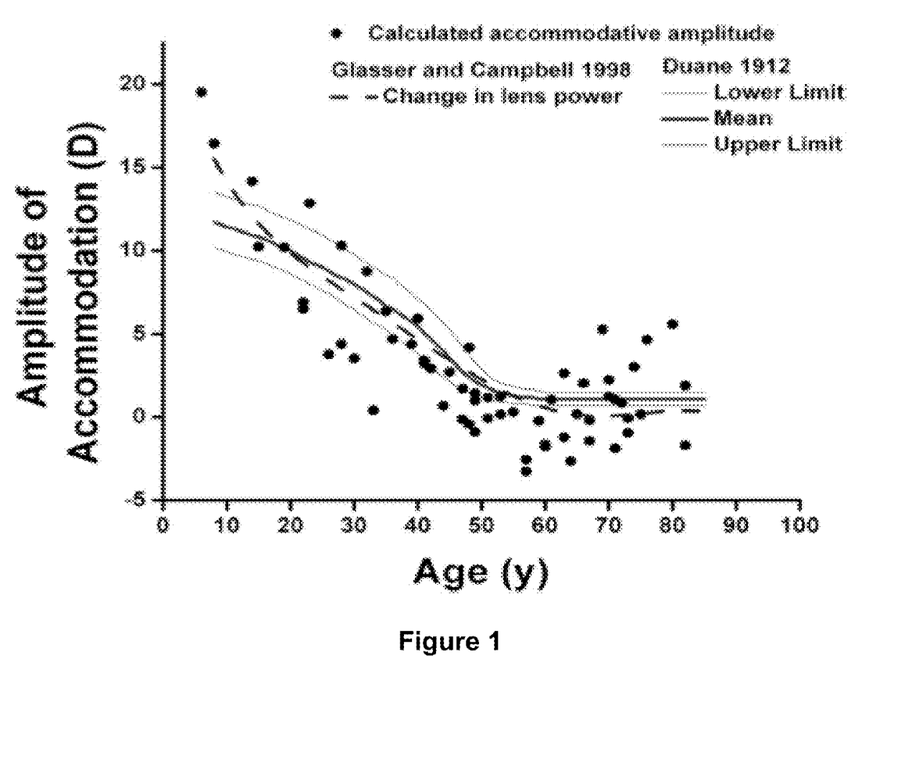
FIG. 1 depicts the accommodative amplitude in diopters (D) of an untreated human lens as a function of age in years. Borja, D et al. 2008. Optical Power of the Isolated Human Crystalline Lens. Invest Opthalmol Vis Sci 49(6):2541-8. Borja et al. calculated the maximum possible accommodative amplitude of each measured lens power data point (n=65). As shown, there is good agreement between the age-dependent loss of accommodation and the maximum amplitude of accommodation calculated from the isolated lens power.

Lens elasticity decreases with age and is a primary diagnostic and causative factor for presbyopia. Lens elasticity can be measured as accommodative amplitude in diopters (D). FIG. 1 depicts the average elasticity in diopters of an untreated human lens as a function of age in years. The lower the value of D, the less elastic the lens. In one embodiment, the agents described herein can decrease and/or maintain D at a value that is greater than the D value exhibited by an untreated lens of about the same age. In other words, the agents can keep accommodative amplitude "above the line" depicted in FIG. 1 (the solid line is mean accommodative amplitude). In one embodiment, D is increased and/or maintained at a value about 2, 5, 7, 10, 15, 25, 50, 100, 150, or 200 percent above the line. However, as individual lenses may differ with respect to average values, another embodiment provides any increase in accommodative amplitude, maintenance of accommodative amplitude, or reduction in the rate of decline of accommodative amplitude (i.e., reduction in the rate of decrease in diopters) for an individual lens compared to the accommodative amplitude of the same lens before treatment. Accordingly, in another embodiment, the methods provide an increase in accommodative amplitude of about 0.25 to about 8 diopters, or at least about 0.1, 0.2, 0.25, 0.5, 1, 1.2, 1.5, 1.8, 2, 2.5, 3, 5, or 8 diopters compared to the same lens before treatment.

Figure 2:
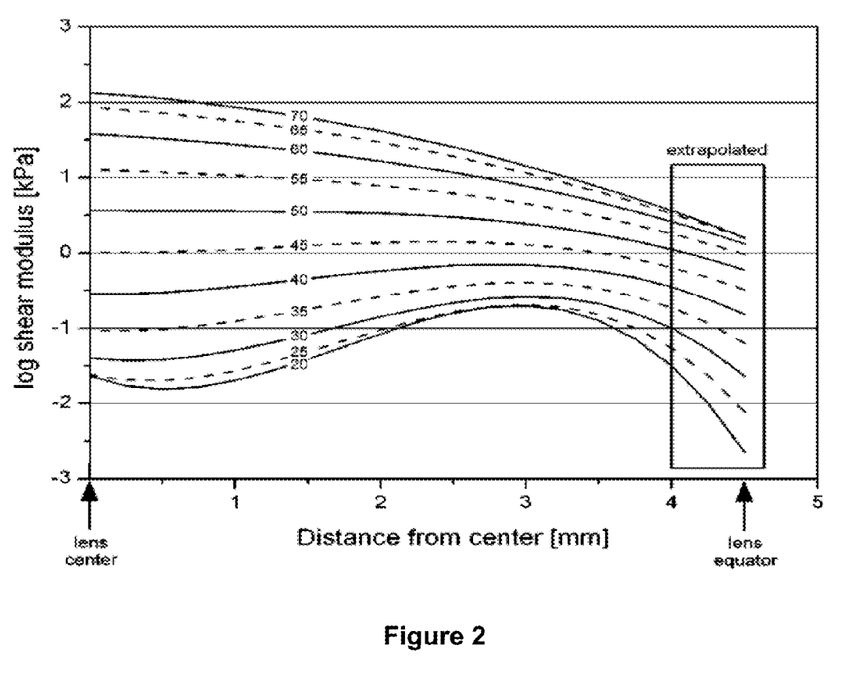
FIG. 2 shows a trend graph of the shear modulus versus position in the lens and age. Weeber, H A et al. 2007. Stiffness gradient in the crystalline lens. Graefes Arch Clin Exp Opthalmol 245(9):1357-66. The line at the bottom is the 20-year-old lens; the line at the top is the 70-year-old lens. The modulus increases with age for all positions in the lens. Measurements were taken up to 4.0 mm from the lens centre. The lines are extrapolated to a radius of 4.5 mm (lens diameter 9.0 mm).

Lens elasticity can also be measured by the unit of elasticity E. The higher the value of E, the less elastic the lens. FIG. 2 depicts the average elasticity (E) of an untreated human lens as a function of age in years. In one embodiment, the agents described herein can decrease and/or maintain E at a value that is less than the E value exhibited by an untreated lens of about the same age. In other words, the agents can keep lens elasticity "below the line" depicted in FIG. 2. In one embodiment, E is decreased and/or maintained at a value about 2, 5, 7, 10, 15, 25, 50, 100, 150, or 200 percent below the line. However, as individual lenses may differ with respect to average values, another embodiment provides any increase in elasticity, maintenance of elasticity, or reduction in the rate of decline of elasticity (i.e., reduction in the rate of increase in E value) for an individual lens compared to the elasticity of the same lens before treatment.

Figure 3:
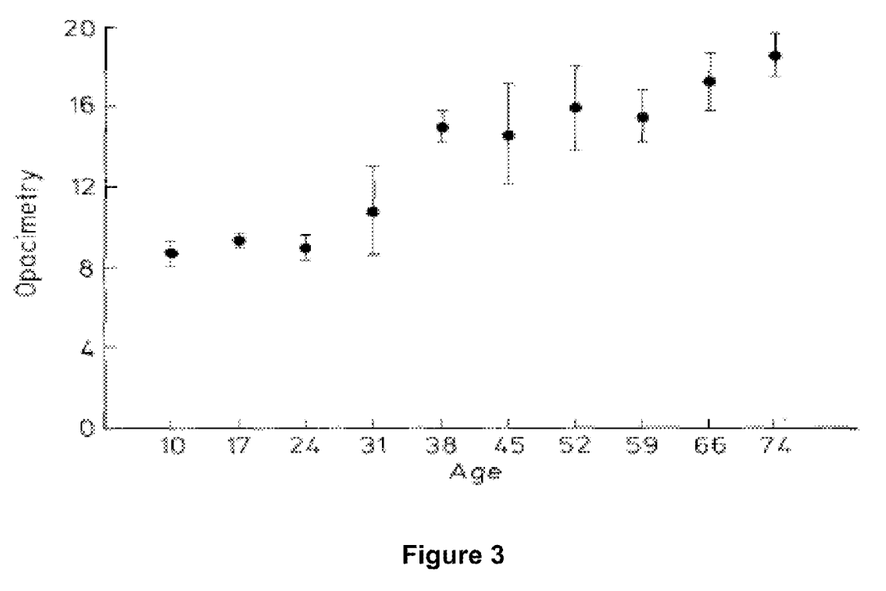

Therapeutic efficacy can also be measured in terms of lens opacity. Lens opacity increases with age and is a primary diagnostic and causative factor for cataract. FIG. 3 depicts the average opacity of an untreated human lens as a function of age in years. In one embodiment, the agents described herein can decrease and/or maintain opacity at a value that is less than the opacity value exhibited by an untreated lens of about the same age. In other words, the agents can keep lens opacity "below the line" depicted in FIG. 3. In one embodiment, lens elasticity is decreased and/or maintained at a value about 2, 5, 7, 10, 15, 25, 50, 100, 150, or 200 percent below the line. However, as individual lenses may differ with respect to average values, another embodiment provides any decrease, maintenance, or reduction in the rate of increase of opacity for an individual lens compared to the opacity of the same lens before treatment.

Therapeutic efficacy can also be measured as a reduction in the rate of cell proliferation, particularly lens epithelial cell proliferation. Thus, in some embodiments, therapeutic efficacy can be measured by cytostatic effect.

Some agents described herein exist naturally in the untreated eye. Lipoic acid and cystine, for example, occur naturally in eye tissue. In general, a therapeutically effective amount of the exogenously administered agent is often at least about 1 or 2 orders of magnitude larger than the natural level of the agent. In one embodiment, the lipoic acid or derivative thereof is administered in a dose amount of up to about 1 mM. In one embodiment, the dose amount of lipoic acid or a derivative thereof is about 1 $\mu$M up to 1 mM, preferably about 0.25 mM to about 0.75 mM, or about 0.5 mM. In another embodiment, the dose amount of lipoic acid or derivative thereof is no more than 0.5 mM, 250 $\mu$M, 100 $\mu$M, 50 $\mu$M, 20 $\mu$M, or 10 $\mu$M. In another embodiment, cystine or a derivative thereof is administered in a dose amount of about 1 $\mu$M to about 20 $\mu$M. In yet another embodiment, the dose amount of cystine or a derivative thereof is no more than 20 $\mu$M, the limit of cystine solubility in aqueous solution, or no more than 15 $\mu$M, 12 $\mu$M, 10 $\mu$M, 7 $\mu$M, or 5 $\mu$M. The dose amount will depend on the route of administration as well as the age and condition of the patient. Similarly, the frequency of dosing will depend on similar factors as can be determined by one of ordinary skill in the art.

Efficacy has been demonstrated in vitro for specific exemplary dosing. FIG. 2 shows that the inelasticity increases by a factor of nearly 20 during the critical period from age 40 to 55 years. From current data, a 10 $\mu$M dose can decrease the inelasticity over 95% within a millimeter volume element (voxel). Extrapolation of these results to a volume element in the human lens suggests that using this treatment dose on a 55 year old person with a 10 kPA lens starting modulus value (see FIG. 2) could be reduced after treatment to a value of about 0.5 kPA (which then corresponds to a value typically seen with a 40 yr old person). FIG. 1 permits a conversion of these modulus values to optical amplitude: accommodative amplitude is normally reduced to almost 0 above 55 years, while a person at 40-45 years still exhibits around 4-5 diopters of accommodation.

The methods include preventative methods that can be performed on patients of any age. The methods also include therapeutic methods that can be performed on patients of any age, particularly patients that are at least 20, 25, 30, 35, 40, 45, 50, 52, 55, 57, 60, 70, 75, or 80 years of age.

The agents described herein can be formulated to achieve any delivery system known in the art such as immediate or sustained release delivery; systemic, ocular, or localized delivery; topical or injection delivery; prodrug or caged delivery systems, e.g., coumarin cages (as described, for example, in co-pending application U.S. Ser. No. 12/267,260), etc.

The agents can be linked to, co-administered with, and/or co-formulated with other therapies such as other pharmaceutically active ingredients and/or energy sources (as described, for example, in co-pending application U.S. Ser. No. 11/946, 659). In one embodiment, the agent is co-administered with chemical energy, such as, for example glucose-6-phosphate (G6P), NADPH, or glucose. In one embodiment, the agent is activated by an endogenous chemical energy, e.g., endogenous glucose. For example, endogenous glucose can activate lipoic acid or a derivative thereof to dihydrolipoic acid (DHLA) or a corresponding derivative thereof.

The agents can be formulated as a pharmaceutically acceptable salt.

The agents can be administered to a lens by any route of administration including, but not limited to, topical, subtenons, subconjunctival, intracameral, intravitreal, or iontophoresis routes. In one embodiment, the agent can be delivered topically, e.g., via an eye drop, gel, ointment, or salve. In other embodiment, the compound can be delivered via an acute delivery system, e.g., using nanotubes, local injection, micro-injection, syringe or scleral deposition, or ultrasound.

The disclosures of all references and publications cited above are expressly incorporated by reference in their entireties.

Any numerical values recited herein include all values from the lower value to the upper value in increments of any measurable degree of precision. For example, if the value of a variable such as age, amount, time, percent increase/decrease and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

Although particular features have been described with respect to particular embodiment as illustrative, one of ordinary skill in the art would recognize that any particular feature could be applied to any of the embodiments described herein. Various modifications and variations of the described agents, compositions, and methods will be apparent to those skilled in the art without departing from the scope and spirit of the invention. To further illustrate particular embodiments of the invention, we provide the following non-limiting examples.

EXAMPLES

Example 1

In Vitro Efficacy Studies

Increase in Elasticity: Pairs of mouse lenses were incubated in medium 200 supplemented with an antibiotic, an antimycotic, in the presence or absence of lipoic acid (concentrations ranging from 0.5 µM to 500 µM) for 8-15 hours. Each lens was removed from medium, weighed, and photographed on a micrometer scale. A coverslip of known weight (0.17899±0.00200 g) was placed on the lens, and the lens was photographed again on the micrometer scale. The diameter of each lens with and without the coverslip was determined from the photographs. The change in lens diameter produced by the force (coverslip) was computed $\Delta D = (D_{withcoverslip} - D_{withoutcoverslip})$. The results (FIG. 4, ‡) indicate that lipoic acid at concentrations≥9.6 µM caused a statistically significant increase in $\Delta D$, $p<0.0001$.

Figure 4:
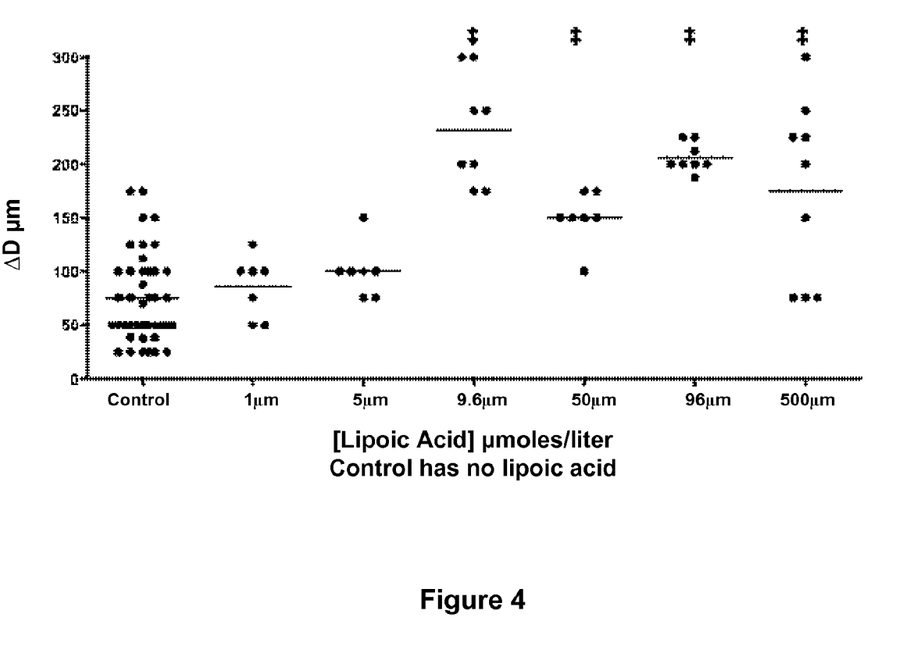
FIG. 4 depicts a scatter plot of the change in ΔD (micrometers) in the absence (control) and presence of lipoic acid in lens organ culture experiments. The symbol ‡ designates significantly larger changes in ΔD when compared to controls. Statistical values are highly significant at p<0.0001 by unpaired t-test and by Kiruskal Wallis test, which compared medians of each data set. The relative change in Young's modulus (E) can be calculated as the cubic value derived from the ΔD of the control divided by the ΔD of the experimental or E fractional change=(ΔD con/ΔDexp)^3.
Figure 5:
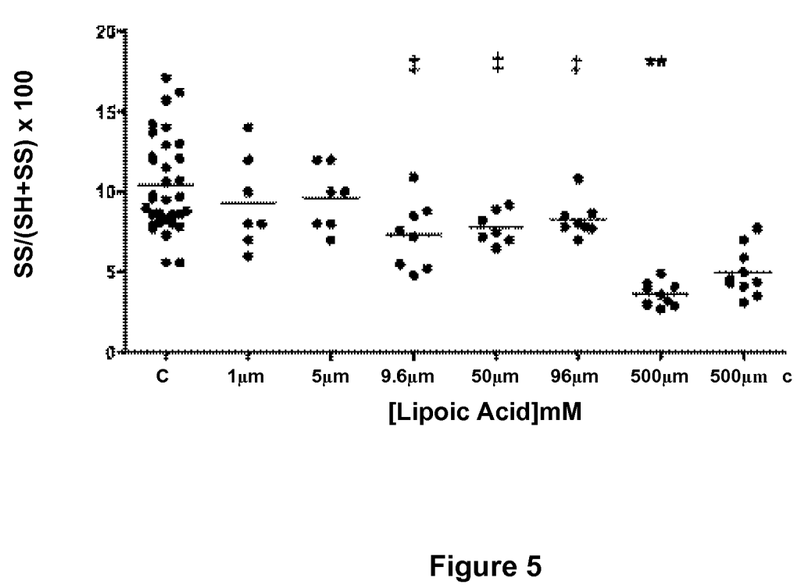

Decrease in disulfide bonds: Lipoic acid at concentrations≥9.6 µM caused a statistically significant decrease in protein disulfides in the mouse lenses where there was a significant increase in $\Delta D$ (FIG. 4). Mouse lenses were homogenized in a denaturing buffer containing a fluorescent alkylating agent to modify the free SH groups. After removing the alkylating agent homogenates were reduced and alkylated with a different fluorescent alkylating agent. Absorption spectra of the modified proteins were used to calculate free protein SH and protein SS groups. The results are shown in FIG. 5.

What is claimed is:

1. A method of treating presbyopia comprising administering an agent including at least two components independently selected from a sulfur atom, a selenium atom, and a sulfonic group, wherein the agent comprises at least one selenium atom.

2. The method of claim 1, wherein the agent is a five- or six-membered heterocycle having two members independently selected from a sulfur atom and a selenium atom.

3. A lipoic acid derivative agent for treating presbyopia having a formula:

wherein at least one of X and Y is sulfur, and the other is sulfur, selenium, or a sulfonic group, and each R group is independently selected from the group consisting of: —H, —OH, —OAc, —OR, —SR, —CO$_2$R, an electron withdrawing group, and a linear or branched C$_{1-18}$ alkane or alkene optionally substituted by one or more substituents selected from the group consisting of ether, ester, carboxylic acid, phosphate, amide, and amine groups.

4. The agent of claim 3, wherein at least one of X and Y is sulfur, and the other is sulfur or selenium.

5. The agent of claim 3, wherein at least one of R$_{1-10}$ is a linear substituent selected from the group consisting of C$_{2-10}$ alkane and C$_{10-18}$ alkene.

6. The agent of claim 5, wherein the linear substituent has a distal terminal that is —COOH, —NH$_2$, —CO$_2$CH$_3$, or —CO$_2$CH$_2$CH$_3$.

7. The agent of claim 6, wherein the linear substituent is —(CH$_2$)$_{2-10}$NH$_2$.

8. The agent of claim 6, wherein the linear substituent is —(CH$_2$)$_{2-10}$CO$_2$H.

* * * * *

UNITED STATES PATENT AND TRADEMARK OFFICE
CERTIFICATE OF CORRECTION

| | | |
|---|---|---|
| PATENT NO. | : 8,647,612 B2 | Page 1 of 1 |
| APPLICATION NO. | : 12/390928 | |
| DATED | : February 11, 2014 | |
| INVENTOR(S) | : Garner et al. | |

It is certified that error appears in the above-identified patent and that said Letters Patent is hereby corrected as shown below:

On the Title Page, under Related U.S. Application Data, please delete the paragraph under Item (63) "Continuation-in-part of application No. 12/267,260, filed on Nov. 7, 2008, and a continuation-in-part of application No. 11/946,659, filed on Nov. 28, 2007, now Pat. No. 8,147,816, which is a continuation-in-part of application No. 11/135,271, filed on May 24, 2005, now Pat. No. 7,914,815, which is a continuation-in-part of application No. 10/050,879, filed on Jan. 18, 2002, now Pat. No. 6,923,955, said application No. 11/946,659 is a continuation-in-part of application No. 11/010,436, filed on Dec. 14, 2004, now Pat. No. 7,935,332, which is a continuation of application No. 10/050,879, said application No. 11/946,659 is a continuation-in-part of application No. 10/969,868, filed on Oct. 22, 2004, now abandoned, which is a continuation-in-part of application No. 10/050,879, which is a continuation-in-part of application No. 09/930,287, filed on Aug. 16, 2001, now abandoned."

Also, under Item (63) Related U.S. Application Data, please replace the paragraph under Item (60) "Provisional application No. 61/033,870, filed on Mar. 5, 2008, provisional application No. 61/060,487, filed on Jun. 11, 2008, provisional application No. 61/077,186, filed on Jul. 1, 2008, provisional application No. 60/861,262, filed on Nov. 28, 2006, provisional application No. 60/907,734, filed on Apr. 16, 2007, provisional application No. 60/924,686, filed on May 29, 2007, provisional application No. 60/574,211, filed on May 26, 2004, provisional application No. 60/262,423, filed on Jan. 19, 2001, provisional application No. 60/225,659, filed on Aug. 16, 2000" with -- Provisional application No. 61/033,870, filed on Mar. 5, 2008, provisional application No. 61/060,487, filed on Jun. 11, 2008, and provisional application No. 61/077,186 filed on Jul. 1, 2008 --.

Signed and Sealed this
Ninth Day of December, 2014

Michelle K. Lee
*Deputy Director of the United States Patent and Trademark Office*